United States Patent [19]

Lundsgaard et al.

[11] Patent Number: 5,366,903

[45] Date of Patent: *Nov. 22, 1994

[54] METHOD OF PHOTOMETRIC IN VITRO DETERMINATION OF THE CONTENT OF AN ANALYTE IN A SAMPLE OF WHOLE BLOOD

[75] Inventors: Finn C. Lundsgaard, Tastrup; Niels-Henrik Jensen, Farum; Willy Andersen, Espergaerde, all of Denmark

[73] Assignee: Radiometer A/S, Copenhagen, Denmark

[*] Notice: The portion of the term of this patent subsequent to Feb. 22, 2011 has been disclaimed.

[21] Appl. No.: 199,858

[22] Filed: Feb. 22, 1994

Related U.S. Application Data

[63] Continuation of Ser. No. 720,531, Jun. 21, 1991, Pat. No. 5,288,646.

[30] Foreign Application Priority Data

Dec. 22, 1988 [DK] Denmark .................. 7162/88

[51] Int. Cl.$^5$ .......................................... G01N 21/03
[52] U.S. Cl. .................................. 436/165; 436/68; 436/164; 422/82.05; 422/82.11; 128/633; 356/39; 356/246; 356/434
[58] Field of Search ............. 422/82.05, 82.06, 82.11; 436/164, 165, 68, 74; 128/633, 634; 356/39, 246, 434

[56] References Cited

U.S. PATENT DOCUMENTS

| | | | |
|---|---|---|---|
| 3,926,521 | 12/1975 | Ginzel | 356/39 |
| 4,339,317 | 7/1982 | Meiattini et al. | 204/400 |
| 4,420,254 | 12/1983 | Smeaton | 356/246 |
| 4,426,451 | 1/1984 | Columbus | 436/518 |
| 4,444,498 | 4/1984 | Heinemann | 356/246 |
| 4,447,150 | 5/1984 | Heinemann | 356/41 |
| 4,454,229 | 1/1984 | Zander et al. | 436/68 |
| 4,496,344 | 1/1985 | Kamstra | 604/90 |
| 4,509,522 | 1/1985 | Manuccia et al. | 128/634 |
| 4,645,744 | 2/1987 | Charlton et al. | 436/74 |
| 4,654,197 | 3/1987 | Lilja et al. | 422/56 |
| 4,657,736 | 4/1987 | Marsoner et al. | 422/56 |
| 4,675,019 | 6/1987 | Bellhouse et al. | 604/408 |
| 4,703,182 | 10/1987 | Kroneis et al. | 250/458.1 |
| 4,737,144 | 4/1988 | Choksi | 604/198 |
| 4,745,279 | 5/1988 | Karkar et al. | 250/343 |
| 4,775,514 | 10/1988 | Barnikol et al. | 422/83 X |
| 4,781,701 | 10/1988 | Geprags | 604/240 |
| 4,810,090 | 3/1989 | Boucher et al. | 356/39 |
| 4,873,993 | 10/1989 | Meserol et al. | 128/760 |
| 4,929,426 | 5/1990 | Bodai et al. | 422/63 |
| 4,940,945 | 7/1990 | Littlejohn et al. | 324/438 |
| 4,997,769 | 3/1991 | Lundsgaard | 436/66 |
| 5,025,798 | 6/1991 | Schindele | 128/771 |
| 5,029,583 | 7/1991 | Meserol et al. | 128/633 |
| 5,046,496 | 9/1991 | Betts et al. | 128/635 |
| 5,064,618 | 11/1991 | Baker et al. | 422/82.01 |
| 5,066,859 | 11/1991 | Karker et al. | 250/339 |
| 5,080,865 | 1/1992 | Leiner et al. | 422/68.1 |
| 5,120,510 | 6/1992 | Gourley et al. | 422/82.07 |
| 5,127,077 | 6/1992 | Iyer et al. | 128/634 X |

FOREIGN PATENT DOCUMENTS 0185126 6/1986 European Pat. Off.

Primary Examiner—James C. Housel
Assistant Examiner—Maureen M. Wallenhorst
Attorney, Agent, or Firm—Bryan Cave

[57] ABSTRACT

A sampling device for photometric determination of the content of an analyte in a sample of whole blood has at least one measuring chamber having two wall parts, at least one wall part being locally transparent, at least one wall part being sufficiently deformable to facilitate displacement of the whole blood sample from the measuring chamber. The measuring chamber also contains a transparent body having a radiation transmission characteristic dependent upon the concentration of a predetermined analyte in the whole blood sample. The sample device is employed in an analyzer for photometric determination of the content of an analyte in a sample of whole blood and in a method of photometric in vitro determination of the content of an analyte in a sample of whole blood. In the method, a sample of whole blood is transferred directly from an in vivo locality to the sampling device, the measuring chamber therein is deformed in a controlled manner to substantially drain the whole blood from the measuring chamber, radiation is transmitted through the substantially drained measuring chamber, detected, and the analyte content determined.

12 Claims, 5 Drawing Sheets

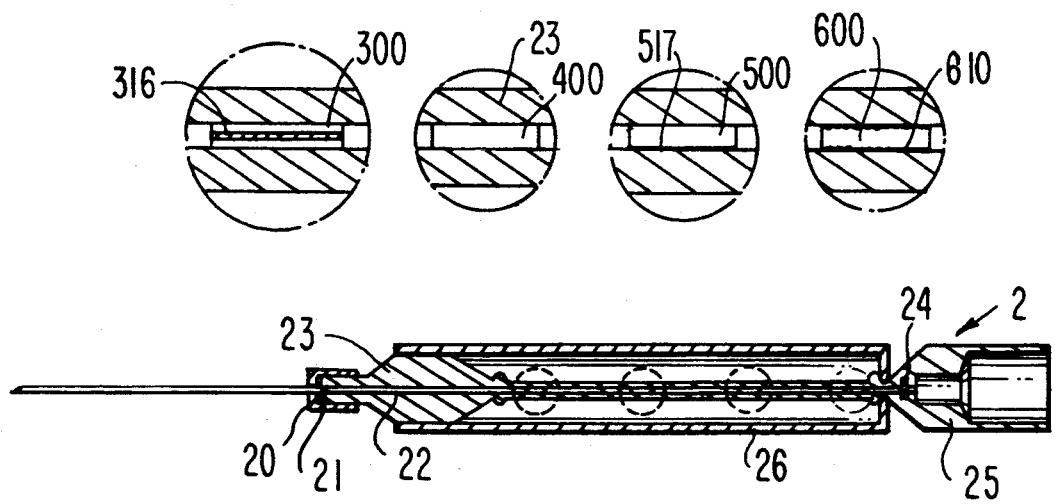
FIG. 3A FIG. 3B FIG. 3C FIG. 3D
FIG. 3
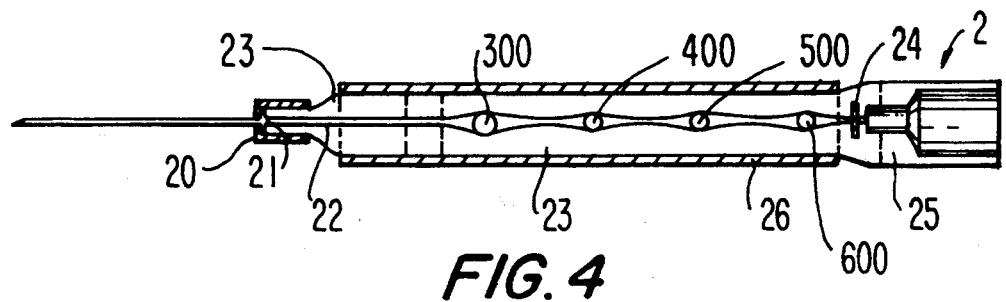
FIG. 4
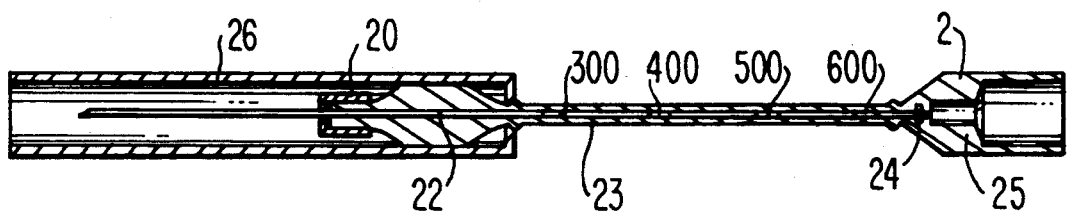
FIG. 5

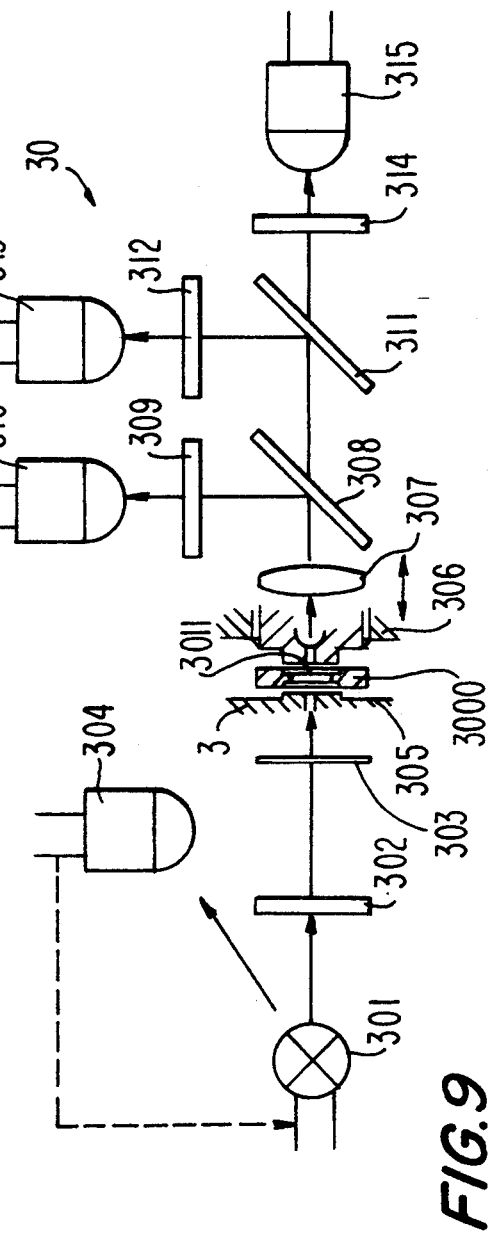
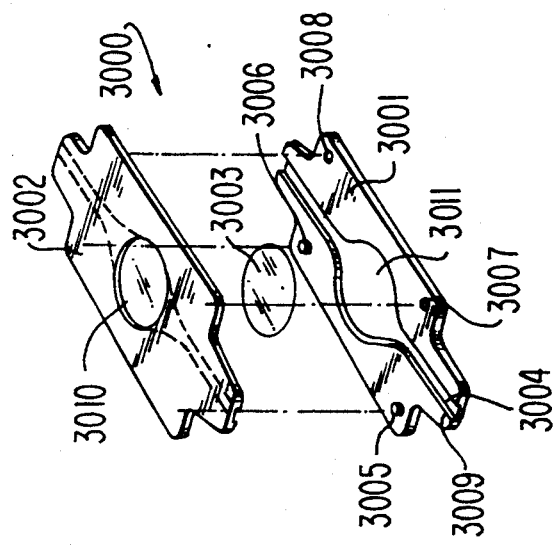
FIG. 8
FIG. 9

METHOD OF PHOTOMETRIC IN VITRO DETERMINATION OF THE CONTENT OF AN ANALYTE IN A SAMPLE OF WHOLE BLOOD

CROSS-REFERENCE TO RELATED APPLICATIONS

This application is a continuation of U.S. application Ser. No. 07/720,531, filed Jun. 21, 1991, now U.S. Pat. No. 5,288,646 issued Feb. 22, 1994.

FIELD OF THE INVENTION

The present invention relates to a method of photometric in vitro determination of the content of an analyte in a sample of whole blood wherein the sample from an in vivo locality is transferred directly to a sampling device comprising a sample container with a measuring chamber with at least locally transparent wall parts and the sample containing sample container is brought into optical communication with an optical system adapted to the analyte comprising a radiation source and a radiation detector arranged downstream to the sample container in the radiation transmission path, and wherein there is provided within the measuring chamber a transparent body, the transmission characteristics of which for radiation transmitted through the sample container vary with the content of analyte in the environment of the body, and wherein subsequently the measuring chamber is deformed in a controlled manner.

BACKGROUND OF THE INVENTION

A number of clinical chemistry analyzers exists which analyzers consist of a combination of disposable components, which are only used for one single analysis operation and only get in touch with one single sample, and an analysing section adapted for receiving the sample containing disposable device and containing the additional components necessary for accomplishing a clinical chemical analysis.

These analyzers all have in common that the transfer of blood sample from patient to disposable device takes place via a separate sampling device such as a syringe, a capillary tube or a vacuum tube sampling device.

In certain cases the sampling device and the disposable device constitute one and the same device. Thus, International patent application WO 86/00138 (Shanks et al.) discloses a device with a cavity sufficiently small for a given sample to be sucked into the cavity by capillary effect.

In this equipment the cavity is provided with an electrode structure and possibly a coating of a material adapted to the analysis to be performed with the equipment. The electrode structure provided in the cavity may i.a. be a potentiometric ion sensitive electrode structure or an amperometric electrode structure. The latter is described in connection with determination of hydrogen peroxide and oxygen in the sample.

Supplementary use of the equipment for optical analysis of the products of a specific binding reaction is also described.

From the specification of Danish patent publication DK 150804 (Lilja, J. E. and Nilsson, S. E. L.) is known a sample container for sampling, mixing a sample with at least one reagent and directly performing a separate optical analysis of the sample mixed with the reagent. The sample container has a capillary cavity coated with a reagent and the inlet to the sample container works by capillary effect. The sample container is stated to be useful for most different kinds of analysis and to be especially advantageous for determination of hemoglobin.

From the specification of British patent application GB 2025065 (Meiattini, F. et. al.) is known a plunger syringe for withdrawal of a blood sample. The blood sample is analysed by means of sensors incorporated in the syringe plunger. It is thereby avoided to transfer the sample to a sample station. The sensors are adapted for connection with an analyzer via conductors for registrating, processing, and outprinting analysis data. The specific sensors described in the specification of the said British patent application GB 2025065 are electrochemical sensors for blood gases and blood electrolytes.

None of the above-mentioned publications which in applicant's opinion represent the prior art closest to the present invention deal with the special problems connected with photometric determination of an analyte in whole blood.

A serious problem when performing a photometric analysis of a particular analyte in whole blood is that the light reduction caused by the remaining components in the sample is extensive as compared to the light reduction attributable to the analyte. Another serious problem is that due to its content of blood cells whole blood gives rise to a light reduction depending on the content of blood cells in the sample, i.e. of the sample hematocrit, and accordingly said light reduction will constitute an unknown factor. Varying content of other components than hematocrit may also result in a light reduction which varies between samples.

SUMMARY OF THE INVENTION

The object of the invention is to provide a method by which the above-mentioned problems connected with photometric analysis of a whole blood sample located in the sample container of a sampling device during the analysis procedure, are readily eliminated.

This is achieved by the method according to the invention which method is characterized by the transparent body is equilibrated with the sample, the controlled deformation of the measuring chamber is carried out so that a substantially complete draining of blood sample from the part of the measuring chamber located in the radiation transmission path is provided, and the analyte content is determined on the basis of detection of radiation transmitted from the radiation source through the deformed, drained measuring chamber and the transparent body to the radiation detector.

BRIEF DESCRIPTION OF THE DRAWINGS

FIGS. 3a-3d are cross-sectional views of the sampling device of FIG. 3.

FIG. 3, FIG. 4 and FIG. 5 are views of a preferred embodiment of a sampling device according to the invention;

FIG. 8 is a perspective view of a sample container for use in determining pH;

FIG. 9 is a partial cross section of an optical unit in a system comprising an analyzer according to the invention and a sampling device according to the invention for photometric determination of pH and with a schematic representation of the components forming parts of the optical unit.

In the different figures like reference numerals designate like parts.

DETAILED DESCRIPTION OF THE INVENTION

Figure 1:
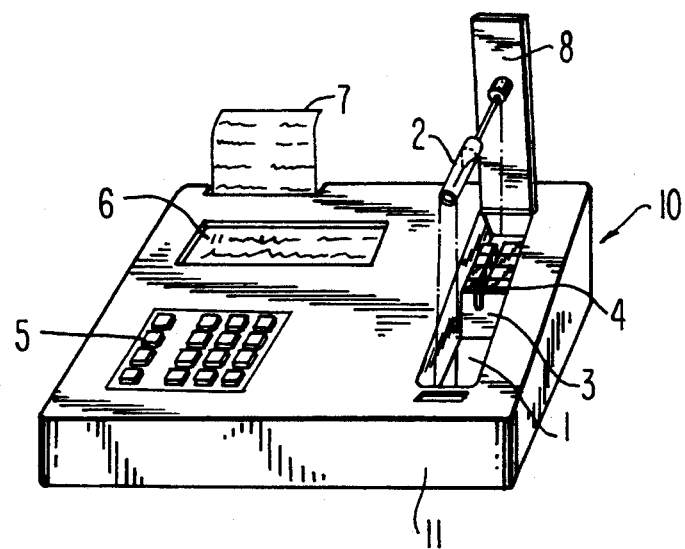
FIG. 1 is a perspective view of a preferred embodiment of an analyzer and a sample container, which together constitute the system according to the invention for photometric in vitro determination of an analyte in a blood sample.

"In vivo locality" denotes in the present context a locality being in direct connection with the blood circulation or being a locality in the blood circulation itself. Sampling by arterial puncture, whereby the blood sample is transferred from the artery to the sample container by a thin needle, as well as via an arterial catheter or via capillary puncture are sampling methodologies, in which the blood sample is transferred directly from an in vivo locality to a sample container.

The radiation emitted from the radiation source may be broad banded as well as monochromatic radiation and may belong to the ultraviolet range, the visible range, the near infrared range and/or the infrared range. The radiation source may comprise one component or several components emitting radiation at their respective particular wavelength range. The radiation detector as well may comprise one component detecting radiation at a particular wavelength range or several components detecting radiation at their respective particular wavelength ranges. The several components of the radiation source may be provided as one integrated device or as separate devices. The same applies to the radiation detector.

The controlled deformation of the sample chamber is a deformation reducing the volume of the measuring chamber to such extent that the measuring chamber is either completely or locally drained for blood sample. By "local draining" is understood that the part of the measuring chamber traversed by the radiation is drained for blood sample.

In a preferred embodiment of the method according to the invention the optical communication is established by placing the sample container in a sample container station of an analyzer.

Alternatively, the optical communication may be established by one or several cables which via means for contacting the sample container and optical fibres establish optical communication between the optical system and the sample container.

The transparent body used in the method according to the present invention is made of a material with a homegeneous structure, in particular a homogeneous surface making the material suited for use in photometric transmission analysis. Preferably, the body is shaped as a disc or plate with two planoparallel surfaces and a thickness of less than 1 mm, preferably 1–500 $\mu$m, in particular 5–250 $\mu$m and most preferably 8–200 $\mu$m.

If an indicator is fixed to the transparent body the indicator may be fixed by any suitable immobilization method such as by absorption, adsorption, ion binding or covalent binding.

Conceivably, it will be possible to make a determination of the content of several analytes in the blood sample within one measuring chamber provided that each individual analyte has an effect on the transmission properties of the transparent body and that each analyte affects the transmission properties differently.

Such determination of several analytes within one measuring chamber may be accomplished by using a transparent body to which several indicators are fixed.

The use of a transparent body containing a reagent which on reaction with the analyte forms a reaction product changing the transmission properties of the body in relation to the analyte concentration in the environment of the body would be suitable for the determination of certain analytes. In that case it may be the reaction product per se which changes the transmission properties of the body or an indicator which is fixed to the body and is affected by the reaction product.

In particular, the method according to the invention aims at such analytes as blood gases, cationic and anionic components in blood (blood electrolytes), metabolites, hormones, enzymes, proteins, drugs and other chemical species which is or may be found in blood. Examples of such analytes are oxygen, carbon dioxide, $H^+$ (or pH), $Li^+$, $Na^+$, $K^+$, $Ca^{++}$, $Mg^{++}$, $Cl^-$, $HCO_3^-$, urea, glucose, creatinine, lactate, bilirubin, cholesterol, triglycerides, and uric acid. Beyond this the invention particularly aims at any analyte mentioned in Mosbach, K., "Methods in Enzymology, Immobilized Enzymes and Cells, Part D", 137 (1988) p. 4–7 and ibid., p. 411.

In connection with determination of the carbon dioxide content is preferred a body made of silicone rubber or another transparent, homogeneous material with a high dissolution power for $CO_2$. The $CO_2$ determination is accomplished on the basis of testing the transmission properties of the body for 4.2 $\mu$m radiation. The basic principles for such determination are disclosed in the specification of British patent application GB 2160646 and in the specification of European patent application EP 253559.

In connection with determination of pH is preferred a body made of a polymer material with —OH groups available for immobilization, e.g. a cellulose or cellophane material, and with a pH indicator which may be covalently bound thereto, e.g. an indicator comprising the reactive group —$SO_2$—$CH_2$—$CH_2$—O—$SO_3H$. Cellophane in particular has physical properties suitable for the present purpose, such as a well-defined thickness and a homogeneous structure.

The invention also relates to a sampling device comprising a sample container with a measuring chamber having at least locally transparent opposite wall parts and having the characteristic features of controlled deformable wall parts that are deformable such that the measuring chamber is substantially drained of blood sample on normal use of the sampling device.

Preferably, the locally transparent wall parts comprise planoparallel parts extending parallel with the planoparallel surfaces of the transparent body. By such configuration is ensured that the drainage of the measuring chamber is readily obtained, viz. by pressing the wall parts against the transparent body. The transparent body may be loosely accomodated in the measuring chamber or it may be fixed to a wall part.

Other preferred embodiments of the sampling device according to the invention have the characteristic features set forth in the dependent claims.

The sample container may comprise one measuring chamber or several measuring chambers disposed in series or in parallel. Preferably the sample container is made of an injection mouldable polymeric base material, e.g. the material sold under the trade name ARNITE ™ from AKZO, Arnheim, Holland.

In connection with the performance of a pH or a carbon dioxide determination on a blood sample in the measuring chamber the wall parts of the measuring chamber are preferably made of a polymer material having a low carbon dioxide permeability and suitable transmission properties for radiation at the wavelengths relevant to the above-mentioned determinations, said wavelengths being discussed at another page. A suitable material is an ethylene vinylalcohol copolymer of the type EVAL-E ™ sold by Kuraray Co., Osaka, Japan.

In the case where the blood sample is provided by capillary puncture, the use of a sample container with a dimension sufficiently small for the sample container to be filled by capillary effect is preferred.

In the case where a sample of arterial blood is desired, the use of a sample container with an inlet located in a coupling means, preferably a Luer cone, for coupling the sample container to a needle or a catheter is preferred.

The invention further comprises an analyzer for use in the method according to the invention, said analyzer having the characteristic features of means further adapted to deform the measuring chamber such that the measuring chamber part located in the radiation transmission path is essentially drained of blood sample.

In a preferred embodiment the analyzer comprises data processing means for processing the registered radiation data for deriving the content of the actual analyte in the actual sample from these. Alternatively the analyzer is adapted for connection to a separate data processing unit.

In a further preferred embodiment of the system according to the invention the analyzer comprises means for displaying the analyte content. Alternatively, the analyzer is adapted for connection with means such as, e.g. a data screen, a display, a printer, or a plotter.

The invention will now be explained in the following with reference to the drawings and the subsequent examples. In the drawings The analysis system shown in FIG. 1 and generally designated 10 is a compact portable "stand-alone" system, which is suited for decentral use, i.e. use outside a regular laboratory environment, e.g. in an operating room or at an intensive ward. The analysis system 10 comprises a blood sampling device 2 for disposable use and used in connection with an analyzer 11. The sampling device 2 is more explicitly described in connection with the description of FIGS. 3–5 below. The sampling device 2 and the analyzer 11 are adapted to interact in the way that the analyzer 11 has a sample container station 1 with an optical section 3 adapted for receiving the sampling device 2 or possibly the sample container of the sampling device, so that the optical communication between the sampling device 2 and the optical components of the optical unit 3, which is necessary for photometric analysis, is obtained.

The sample container station 1 can be closed by a cover 8, which is closed after placing the sampling device 2 in the station. By closing the cover 8 different mechanisms are activated, e.g. a not shown clamping mechanism, which secures the sampling device 2 in the optical section 3 and at the same time thermostatically controls the sampling device to a desired temperature, preferably app. 37° C.

Closing the cover 8 further results in a signal being sent to the controlling unit of the analyzer and indicating the start of an analysis procedure. An operator can control the operation of the analyzer by means of a keyboard 5 and a display 6. The analyzer 11 preferably also comprises a printer, which can produce an outprint 7 of i.a. the analysis results obtained by the analyzer.

After placing the sampling device 2 in the sample container station 1 and closing the cover 8 of this, the optical components comprising of radiation sources and radiation detectors are activated, whereupon the analyzer 11 calculates one or several parameters on the basis of the signals from the radiation detectors. The result of the calculations is displayed on the display 6 and is printed on the paper outprint 7 by the printer. When the calculations are terminated and the results displayed and/or printed out the cover 8 is opened and the sampling device 2 is displaced from the sample container station 1 and disposed of.

Figure 2:
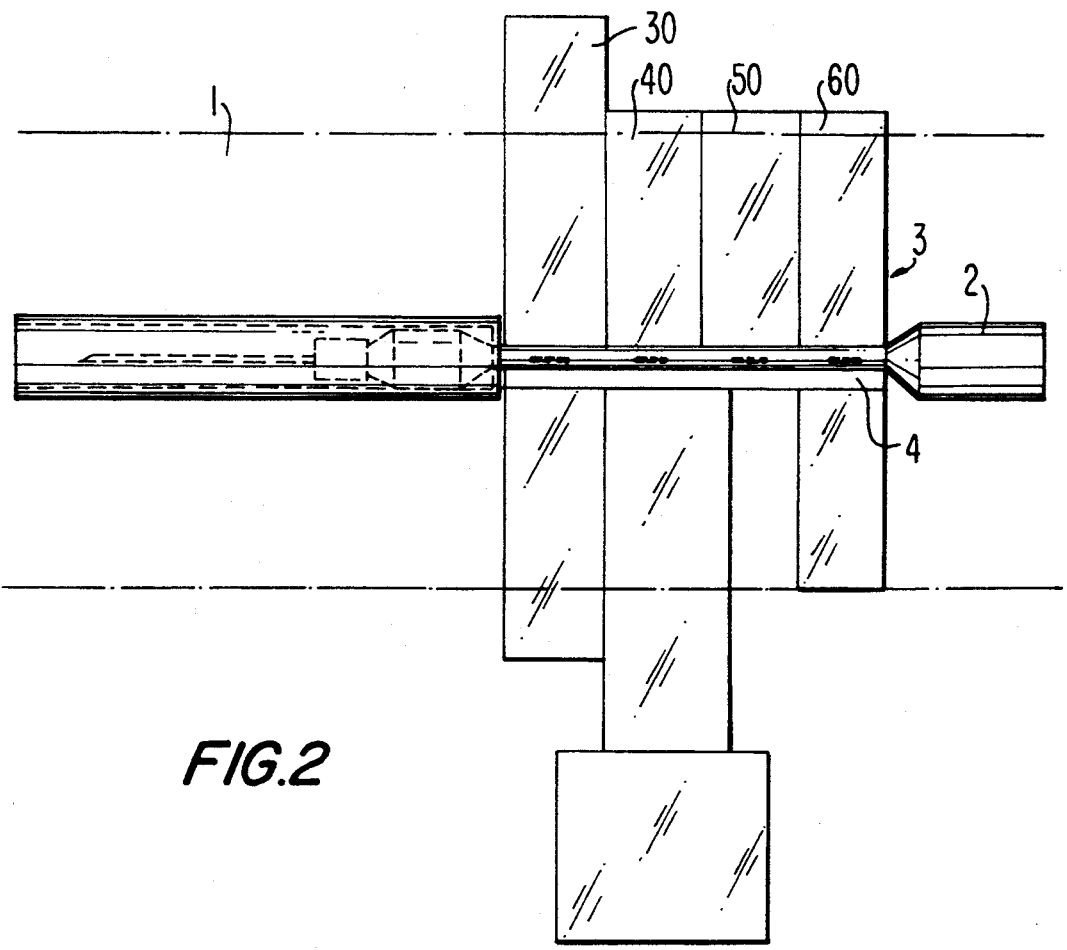
FIG. 2 is an enlarged schematic view from above of the sample container station of the analyzer with the sampling device.

In a larger scale FIG. 2 shows a partially schematic section of the sample container station 1 viewed from above. As shown the optical section 3 comprises four optical units 30, 40, 50, and 60 adapted for determination of pH (unit 30), carbon dioxide (unit 40), oxygen (unit 50) and hemoglobin and oxygen saturation (unit 60) respectively. The sample container of the sampling device with four measuring chambers is placed in a slot 4 in the optical section 3.

Even though the analyzer 11 is shown containing four optical units it can in principle contain an arbitrary number and/or an arbitrary combination of units beyond the unit utilized in the method according to the invention.

FIG. 3 shows a longitudinal section of the sampling device 2 and four segments of this in a larger scale. The sampling device comprises a body 23, which at least in specified areas is made of a material transparent for the relevant radiation. The body 23 has a continuous conduit 22 locally extended for forming measuring chambers 300, 400, 500, and 600. During a course of measurement the actual blood sample fills the conduit 22 from its inlet aperture 21 to a hydrophobic filter 24 placed behind the measuring chambers. The section of the body 23 surrounding the inlet aperture is provided with a Luer cone and is therefore suitable for being mounted with a needle 20 of the type normally used for blood sampling. The section 25 of the body 23 pointing away from the inlet aperture is adapted for coupling with a traditional plunger syringe. Such a plunger syringe is used as aid at the sampling in certain situations, e.g. when the patient, whose blood gas parameters are to be determined, has a very low blood pressure.

When the sampling device 2 is placed correctly in the sample container station 1, the measuring chambers 300, 400, 500, and 600 communicate optically with the optical units 30, 40, 50, and 60. The measuring chamber 300 optically communicating with the optical unit 30 is adapted for determination of pH in the blood sample and contains a cellophane membrane 316, to which is immobilized a pH absorbance indicator. When the indicator is in chemical equilibrium with the blood sample, the ratio between the acid form of the indicator and the basic form of the indicator reflects the pH value of the blood sample. The chemical and photometric basis for the pH determination appears from FIG. 7, 8, and 9 and of the description of these. An embodiment of the optical unit 30 appears from FIG. 9 and the description of this.

Finally it appears from FIG. 3 that the sampling device 2 has an integral needle protecting means 26. In the embodiment shown the needle protecting means 26 is a tubular jacket movable in the axial direction of the sample container between a first position, wherein the jacket exposes the point of the needle, and a second position, wherein the jacket surrounds the point of the needle.

FIG. 3 shows the protecting jacket 26 in the first position, in which it is placed at the sampling moment.

FIG. 4 shows a longitudinal section of the sampling device. The section is placed perpendicular to the section shown in FIG. 3.

The sample container body 23 consists of two halves, of which only one is seen in FIG. 4.

FIG. 5 shows finally the same section as FIG. 3 but in FIG. 5 the protecting jacket is displaced to the second position, wherein it surrounds the point of the needle. The jacket 26 is displaced to this second position immediately after the sampling.

Figure 6:
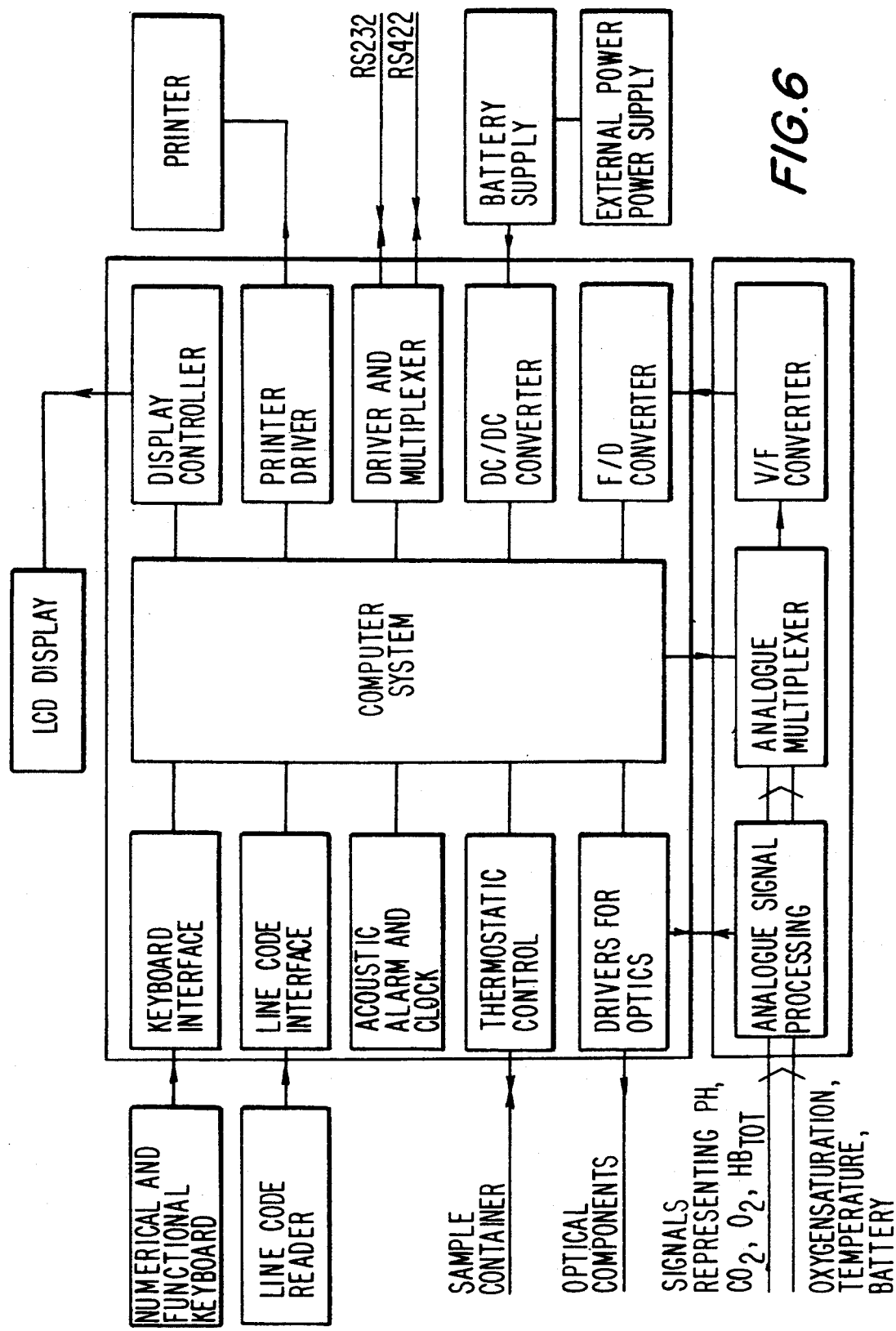
FIG. 6 is an electric block diagram of the analyzer shown in FIG. 1.

FIG. 6 shows the electrical block diagram for the analyzer 11 and speaks for itself.

Figure 7:
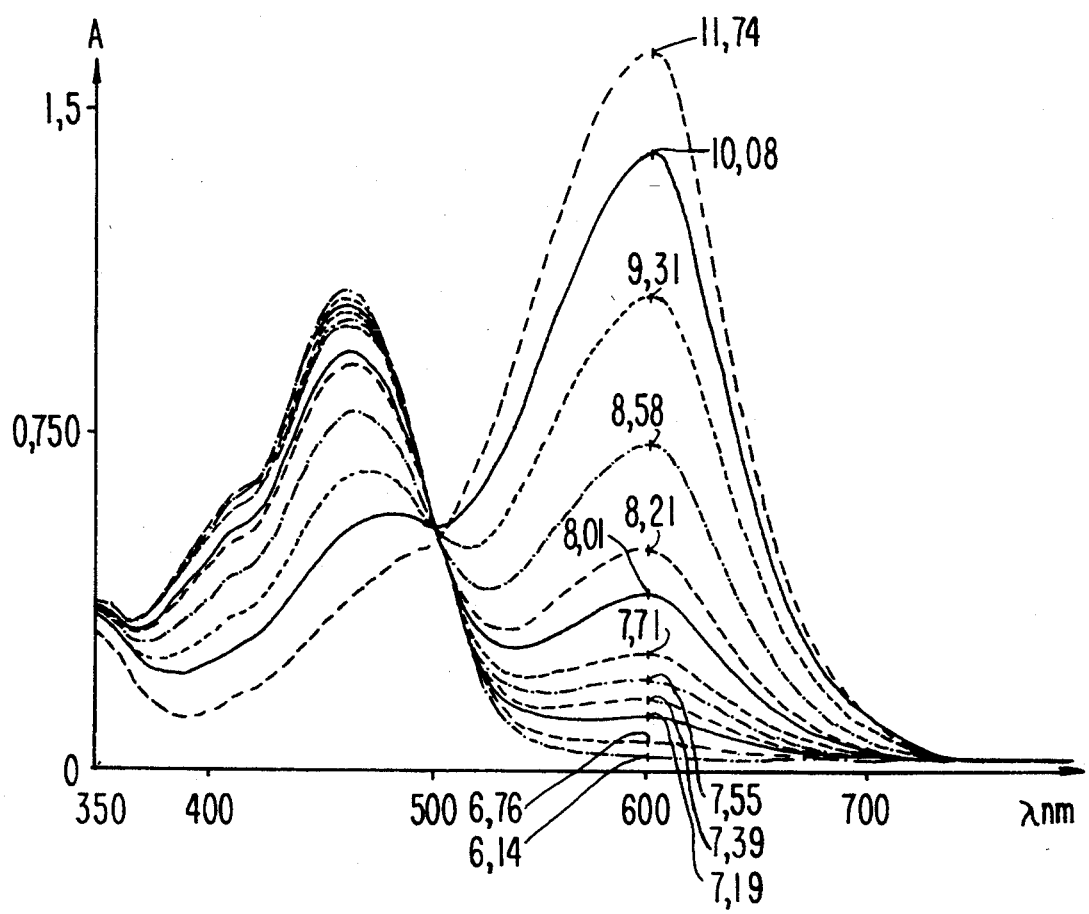
FIG. 7 shows the photometric basis for determination of pH.

FIG. 7 shows the absorption spectrum for a pH absorption indicator N-9 more closely described below in connection with FIG. 8. The indicator is immobilized to a cellophane membrane by the method also described in detail in connection with FIG. 8. The spectrum is recorded by a spectrophotometer of the type Shimadzu Spectrophotometer UV 250. The absorption measurements were performed on a cellophane membrane (6×12×0.028 mm) with immobilized indicator. The cellophane was placed in the cuvette of the spectrophotometer in a holder adapted thereto and with dimensions adapted to the dimensions of the cuvette.

In order to determine the absorption conditions at different pH-values, a number of pH buffers with pH values in the pH range from pH 6.14-11.74 was produced. Each buffer consisted of 500 ml 0.1M $KH_2PO_4$ to which was added the necessary amount of 0.1M NaOH. The pH value of each buffer was potentiometrically measured (Radiometer PHM80) by means of a glass electrode (Radiometer GK2402C).

It appears from the spectrum shown in FIG. 7 that the acid form of the indicator has an absorption top at 458 nm and that the basic form of the indicator has an absorption top at 595 nm and that the indicator not substantially absorbs radiation at wavelengths above 750 nm.

FIG. 8 shows an embodiment of a sample container for use in determination of pH in a blood sample. The sample container generally designated 3000, is intended to interact with an analyzer with an optical unit as the one more closely described below in connection with FIG. 9. The sample container consists of two halves 3001 and 3002. These halves are made from a transparent plastic material, e.g. softened polymethyl methacrylate of the type DEGALAN TM SZ70 (Superlos, Copenhagen, Denmark). The two halves are assembled by pins 3005 and 3006 in the half 3001 engaging corresponding, not shown recesses in the half 3002, while not shown pins in this engage recesses 3007 and 3008 in the half 3001. The two halves are hereafter welded together by ultrasonic welding. The line 3009 of material outlined on the lower half 3001 shown in the figure forms a welding seam after the welding. This line of material lies along the edge of a longitudinal conduit 3004, which centrally expands transversely and forms a measuring chamber 3011. A wall section 3010 of the upper half 3002 shown in the figure is elastically deformable and for that reason has a very reduced wall thickness compared to the rest of the half. As mentioned in connection with FIG. 7 a cellophane membrane 3003, to which there is immobilized a pH indicator, is placed in the measuring chamber 3011.

Preparation of the Cellophane Membrane with Immobilized pH Indicator

The pH indicator is delivered by Merck, Darmstadt, West Germany under the name N-9 and is known to contain the reactive group

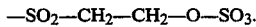
$$-SO_2-CH_2-CH_2-O-SO_3.$$

The immobilisation of the indicator to the membrane takes place in a process, whereby the above mentioned reactive group is transformed with sodium hydroxide into a vinyl sulphone group, which can be coupled to cellophane previously activated by conditioning the cellophane in 0.1M NaOH for 15 minutes.

The reaction scheme describing the coupling reaction between the indicator and the cellophane membrane is:

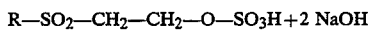
$$R-SO_2-CH_2-CH_2-O-SO_3H + 2\ NaOH$$

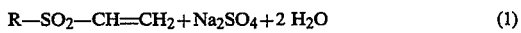
$$R-SO_2-CH=CH_2 + Na_2SO_4 + 2\ H_2O \quad (1)$$

$$R-SO_2-CH=CH_2 + HO\text{-cellophane}$$

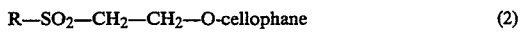
$$R-SO_2-CH_2-CH_2-O\text{-cellophane} \quad (2)$$

R here designates an aryl group.

The quantitative immobilisation procedure is the following:

100 mg cellophane (of the type 113650-36/32 from Struers, Copenhagen, Denmark) is after the above mentioned conditioning with NaOH prepared with an indicator solution consisting of 6 mg N-9, 1000 mg NaCl, 500 mg $Na_2CO_3$, 200 μl 8M NaOH in 40 ml $H_2O$. The cellophane is left in the indicator solution for 30 minutes. Hereafter the cellophane is removed from the indicator solution and washed several times with deionized water, whereafter it is left in deionized water at least through the night before use. The prepared membrane is then kept in deionized water until use.

FIG. 9 shows a prototype of an optical unit 30 for use in determination of pH in a blood sample. The blood sample is located in the measuring chamber 3011 in the sample container 3000, which is secured between a stationary part 305 and a moving part 306. The previously mentioned membrane with immobilized pH-indicator is provided in the measuring chamber. Before the measuring, the blood is pressed away from the measuring chamber by pressing the moving part 306 against the adjacent wall of the measuring chamber 3011. Pressing out the blood sample from the measuring chamber results in the transmission conditions inside the measuring chamber not being influenced by the blood sample itself.

The optical unit 30 works in following way: A radiation source 301 in the form of a halogen lamp with a built-in lens of the type LNS-SE6-560 from Hamai Electric Lamp Co. TTD, Tokyo, Japan emits a parallel beam of broad-banded radiation. This radiation is transmitted to a heat absorbing filter 302 of the type KG 5 from Schott, Mainz, West Germany. This filter eliminates radiation from the infrared range. The radiation is transmitted from the filter to a depolarizer 303 and from there through the measuring chamber 3011. A silicon photodiode 304 of the type SFH 212 from Siemens, Munich, West Germany, receives radiation reflected from different surfaces inside the optical unit and is coupled to the radiation source 301 and ensures constant radiation intensity from this.

After passage of the measuring chamber 3011, the radiation is focused by a lens 307 ($\phi$ 12 mm; f 12 mm; Thermooptik Arnold GmbH & Co., Wellburg, West Germany) onto three silicon photodiodes 310, 313 and 315, which are all of the type SFH 212 and situated in the focal plane of the lens 307. From the lens 307 the radiation is transmitted to a dichroic mirror 308 reflecting radiation of wavelengths less than 560 mm and transmitting radiation of longer wavelengths. The dichroic mirror is delivered by Optisk Laboratorium, Technical University of Denmark, Lyngby, Denmark. The short-waved part of the radiation passes through a band-pass filter 309 (centre value 458 nm; half band width 5.1 nm; Ferroperm, Vedbaek, Denmark) and is transmitted from the band-pass filter 309 to a silicon photodiode 310 of the type SFH 212. The part of the radiation from the lens 307 transmitted through the dichroic mirror 308 is transmitted to another dichroic mirror 311 reflecting radiation of wavelengths less than 690 nm and transmitting the more long-waved radiation. The dichroic mirror is again delivered by Optisk Laboratorium, Technical University of Denmark, Lyngby, Denmark. The reflected radiation is transmitted from the dichroic mirror 311 through a bandpass filter 312 (centre value 589 nm, half band width 14.8 nm; Ferroperm, Vedbaek, Denmark) and from there to a silicon photodiode 313 of the type SFH 212. The radiation transmitted through the dichroic mirror 311 is transmitted from here to a bandpass filter 314 (centre value 750 nm; half band width 10 nm; Ferroperm, Vedbaek, Denmark) and from there to a silicon photodiode 315 of the type SFH 212. The silicon photodiodes 310, 313 and 315 emit a current signal representing the intensity of 458 nm, 589 nm and 760 nm radiation, respectively. On the basis of these radiation intensities the pH value of the sample is calculated.

More precisely the pH value of the sample is calculated in the following way:

With different samples in the form of blood sample as well as the below mentioned two pH buffers in the sample container is for each wavelength $\lambda_1$, $\lambda_2$, $\lambda_3$ determined the current $I_{background,\lambda}$ measured on the corresponding photodiode for a sample container containing a cellophane membrane without immobilized indicator (i.e. a clear cellophane membrane) and sample. This current corresponds to $I_0$ (cf. Lambert Beer's Law).

From the knowledge of the dynamic range of the amplifier for the individual photodiode the current $I_{background,\lambda}$ can be related to the absorbance $A_{background,\lambda}$ as $$A_{background,\lambda} = k \cdot \log I_{background,\lambda}$$

where k is a constant.

In the measuring situation where the sample container contains a cellophane membrane prepared with pH indicator, the current $I_{measurement,\lambda}$ also relating to $A_{measurement,\lambda}$ is determined, whereupon the "true" absorbance at the wavelength $\lambda$ is determined as $$A_\lambda = A_{measurement,\lambda} - A_{background,\lambda}$$

cf. $A = \log I - \log I_0$.

To correct further for drift in the optical system, unclear sample containers or other variations not directly relating to the pH determination, the absorbances $A_{\lambda 1}$ and $A_{\lambda 2}$ are corrected with $A_{\lambda 3}$, and the "new" absorbance values are designated $A'_{\lambda 1}$ and $A'_{\lambda 2}$.

The relation to Lambert Beer's Law hereafter appears as:

$$A'_{\lambda 1} = A_{\lambda 1} - A_{\lambda 3} = \epsilon_{\lambda 1, HIn} \cdot c_{HIn} \cdot 1 + \epsilon_{\lambda 1, In^-} \cdot c_{In^-} \cdot 1$$

$$A'_{\lambda 2} = A_{\lambda 2} - A_{\lambda 3} = \epsilon_{\lambda 2, HIn} \cdot c_{HIn} \cdot 1 + \epsilon_{\lambda 2, In^-} \cdot c_{In^-} \cdot 1 \quad (3)$$

where HIn designates the acid form of the pH indicator, $In^-$ designates the basic form of the indicator, $c_{HIn}$ and $c_{In^-}$ the concentration of the acid and the basic form, respectively, of the indicator, $\epsilon$ the extinction coefficient for the wavelength and compound defined by the suffix, and l the pathlength of the radiation through the sample, which can be inverted to:

$$c_{HIn} = k_{11} A'_{\lambda 1} + k_{12} A'_{\lambda 2}$$

$$c_{In^-} = k_{21} A'_{\lambda 1} + k_{22} A'_{\lambda 2} \quad (4)$$

The constants $k_{11}$, $k_{12}$, $k_{21}$, and $k_{22}$ are determined by measuring $A_{\lambda 1}$, $A_{\lambda 2}$ and $A_{\lambda 3}$ with two pH buffers with known pH values as samples. For each of these pH buffers the proportion $c_{In^-}/c_{HIn}$ is determined according to the Henderson Hasselbalch equation:

$$pH = pk_a + \log[c_{In^-}/c_{HIn}] \quad (5)$$

It is further supposed that $c_{In^-}$ and $c_{HIn}$ can be sets of connected values of $c_{In^-}$ and $c_{Hin}$ can be calculated. If the corrected absorbance values are inserted in the equation set (4), four equations with the four unknown quantities $k_{11}$, $k_{12}$, $k_{21}$, and $k_{22}$ are obtained, and subsequently these four quantities can be calculated.

By measuring unknown samples it is hereafter possible to determine $c_{Hin}$ and $c_{In^-}$ from the equation set (4) and subsequently pH from equation (5).

With respect to the dimensions of the sampling device it is noted that the measuring chamber preferably has a volume of 1–50 $\mu$l, more preferably 5–25 $\mu$l and in particular 7–12 $\mu$l and that the initial distance between the transparent wall parts of the measuring chamber before the drainage for blood sample is preferably less than 1 mm, in particular 200–700 $\mu$m. Further, is noted that after drainage a distance between the transparent wall parts in the region of the radiation transmission path is preferably 5–600 $\mu$m, in particular 8–300 $\mu$m and most preferably 10–200 $\mu$m.

We claim:

1. A sampling device for photometric determination of the content of an analyte in a sample of whole blood, comprising:

at least one measuring chamber which has two wall parts located opposite one another, at least one of the wall parts being locally transparent, at least one of the wall parts being sufficiently deformable to facilitate displacement of the whole blood sample from the at least one measuring chamber, the at least one measuring chamber further including a transparent body disposed between the wall parts, the transparent body being capable of selectively absorbing the analyte or reacting with the analyte such that upon contact of the analyte with the transparent body, a detectable radiation modification is caused in the transparent body which is dependent upon the concentration of the analyte in the whole blood sample, wherein the transparent body maintains the radiation modification after displacement of the whole blood sample from the at least one measuring chamber so that photometric analysis of the analyte in the absence of the whole blood sample can be performed.

2. An analyzer for photometric determination of the content of an analyte in a sample of whole blood comprising:
   a) a radiation source;
   b) means for detecting radiation transmitted from the radiation source;
   c) a sampling device comprising:
      at least one measuring chamber which has two wall parts located opposite one another, at least one of the wall parts being locally transparent, at least one of the wall parts being sufficiently deformable to facilitate displacement of the whole blood sample from the at least one measuring chamber for photometric analysis,
      the at least one measuring chamber further including a transparent body disposed between the wall parts, the transparent body being capable of selectively absorbing the analyte or reacting with the analyte such that upon contact of the analyte with the transparent body, a detectable radiation modification is caused in the transparent body which is dependent upon the concentration of the analyte in the whole blood sample, wherein the transparent body maintains the radiation modification after displacement of the whole blood sample from the at least one measuring chamber so that photometric analysis of the analyte in the absence of the whole blood sample can be performed;
   d) a sampling device station containing the sampling device; and
   e) means for deforming the wall parts of the at least one measuring chamber in the sampling device in a controlled manner to reduce the volume of the at least one measuring chamber such that the sample of whole blood is substantially drained from the at least one measuring chamber, wherein the sampling device station of step (d) is arranged relative to the radiation source and the radiation detection means so that the radiation transmitted from the radiation source will pass through the at least one volume-reduced measuring chamber to the radiation detection means.

3. A method of photometric determination of the content of an analyte in a sample of whole blood, comprising the steps of:
   a) transferring a sample of whole blood directly from an in vivo locality to a sampling device, wherein the sampling device comprises:
      at least one measuring chamber which has two wall parts located opposite one another, at least one of the wall parts being locally transparent, at least one of the wall parts being sufficiently deformable to facilitate displacement of the whole blood sample from the at least one measuring chamber for photometric analysis,
      the at least one measuring chamber further including a transparent body disposed between the wall parts, the transparent body being capable of selectively absorbing the analyte or reacting with the analyte such that upon contact of the analyte with the transparent body a detectable radiation modification is caused in the transparent body which is dependent upon the concentration of the analyte in the whole blood sample, wherein the transparent body maintains the radiation modification after displacement of the whole blood sample from the at least one measuring chamber so that photometric analysis of the analyte in the absence of the whole blood sample can be performed;
   b) placing the sampling device in a sampling device station wherein the sampling device station is arranged relative to an optical system comprising a radiation source and a means for detecting radiation, such that the sampling device is located between the radiation source and the radiation detection means;
   c) deforming the at least one measuring chamber of the sampling device in a controlled manner to reduce the volume of the at least one measuring chamber, thereby substantially draining the sample of whole blood from the measuring chamber;
   d) transmitting radiation from the radiation source through the deformed, substantially drained at least one measuring chamber to the radiation detector;
   e) detecting the radiation transmitted in step d); and
   f) determining the analyte content of the sample of whole blood from the radiation detected in step e).

4. A measuring chamber for photometric determination of the content of an analyte in a sample of whole blood, comprising:
   two wall parts located opposite one another, at least one of the wall parts being locally transparent, at least one of the wall parts being sufficiently deformable to facilitate displacement of the whole blood sample from the measuring chamber for photometric analysis,
   the measuring chamber further including a transparent body disposed between the wall parts, the transparent body being capable of selectively absorbing the analyte or reacting with the analyte such that upon contact of the analyte with the transparent body, a detectable radiation modification is caused in the transparent body which is dependent upon the concentration of the analyte in the whole blood sample, wherein the transparent body maintains the radiation modification after displacement of the whole blood sample from the at least one measuring chamber so that photometric analysis of the analyte in the absence of the whole blood sample can be performed.

5. An analyzer for photometric determination of the content of an analyte in a sample of whole blood, comprising:
   a) a radiation source;
   b) means for detecting radiation transmitted from the radiation source;
   c) at least one measuring chamber which has two wall parts located opposite one another, at least one of the wall parts being locally transparent, at least one of the two wall parts being sufficiently deformable to facilitate displacement of the whole blood sample from the at least one measuring chamber for photometric analysis, the at least one measuring chamber further including a transparent body disposed between the wall parts, the transparent body being capable of selectively absorbing the analyte or reacting with the analyte such that upon contact of the analyte with the transparent body, a detectable radiation modification is caused in the transparent body which is dependent upon the concentration of the analyte in the whole blood sample, wherein the transparent body maintains the radiation modification after displacement of the whole blood sample from the at least one measuring chamber so that photometric analysis of the analyte in the absence of the whole blood sample can be performed, wherein the at least one measuring chamber is arranged relative to the radiation source and the radiation detection means so that the radiation transmitted from the radiation source will pass through the at least one measuring chamber to the radiation detection means; and d) means for deforming at least one of the wall parts of the at least one measuring chamber in a controlled manner to reduce the volume of the at least one measuring chamber such that the sample of whole blood is substantially drained from the at least one measuring chamber.

6. A method of photometric in vitro determination of the content of an analyte in a sample of whole blood, comprising the steps of:

a) transferring a sample of whole blood to a measuring chamber which has two wall parts located opposite one another, at least one of the wall parts being locally transparent, at least one of the wall parts being sufficiently deformable to facilitate displacement of the whole blood sample from the measuring chamber for photometric analysis, the measuring chamber further including a transparent body disposed between the wall parts, the transparent body being capable of selectively absorbing the analyte or reacting with the analyte such that upon contact of the analyte with the transparent body a detectable radiation modification is caused in the transparent body which is dependent upon the concentration of the analyte in the whole blood sample, wherein the transparent body maintains the detectable radiation modification after displacement of the whole blood sample from the measuring chamber so that photometric analysis of the analyte in the absence of the whole blood sample can be performed, the measuring chamber being arranged relative to an optical system comprised of a radiation source and a means for detecting radiation such that the measuring chamber is located between the radiation source and the radiation detection means;

b) deforming the measuring chamber in a controlled manner to reduce the volume of the measuring chamber thereby substantially draining the sample of whole blood from the measuring chamber;

c) transmitting radiation from the radiation source through the deformed, substantially drained measuring chamber to the radiation detector;

d) detecting the radiation transmitted in step c); and e) determining the analyte content of the sample of whole blood from the radiation detected in step d).

7. A sampling device for photometric determination of the content of an analyte in a sample of whole blood, comprising:

at least one measuring chamber which has two wall parts located opposite one another, at least one of the wall parts being locally transparent, at least one of the wall parts being sufficiently deformable to facilitate displacement of the whole blood sample from the at least one measuring chamber, the at least one measuring chamber further including a transparent body disposed between the wall parts, the transparent body being capable of selectively absorbing the analyte or reacting with the analyte such that upon contact of the analyte with the transparent body, a detectable change in a radiation transmission characteristic of the transparent body occurs which is dependent upon the concentration of the analyte in the whole blood sample, wherein the transparent body maintains the changed radiation transmission characteristic after displacement of the whole blood sample from the at least one measuring chamber so that photometric analysis of the analyte in the absence of the whole blood sample can be performed.

8. An analyzer for photometric determination of the content of an analyte in a sample of whole blood comprising:

a) a radiation source;

b) means for detecting radiation transmitted from the radiation source;

c) a sampling device comprising:

at least one measuring chamber which has two wall parts located opposite one another, at least one of the wall parts being locally transparent, at least one of the wall parts being sufficiently deformable to facilitate displacement of the whole blood sample from the at least one measuring chamber for photometric analysis, the at least one measuring chamber further including a transparent body disposed between the wall parts, the transparent body being capable of selectively absorbing the analyte or reacting with the analyte such that upon contact of the analyte with the transparent body, a detectable change in a radiation transmission characteristic of the transparent body occurs which is dependent upon the concentration of the analyte in the whole blood sample, wherein the transparent body maintains the changed radiation transmission characteristic after displacement of the whole blood sample from the at least one measuring chamber so that photometric analysis of the analyte in the absence of the whole blood sample can be performed;

d) a sampling device station containing the sampling device; and e) means for deforming the wall parts of the at least one measuring chamber in the sampling device in a controlled manner to reduce the volume of the at least one measuring chamber such that the sample of whole blood is substantially drained from the at least one measuring chamber, wherein the sampling device station of step (d) is arranged relative to the radiation source and the radiation detection means so that the radiation transmitted from the radiation source will pass through the at least one volume-reduced measuring chamber to the radiation detection means.

9. A method of photometric determination of the content of an analyte in a sample of whole blood, comprising the steps of:
   a) transferring a sample of whole blood directly from an in vivo locality to a sampling device, wherein the sampling device comprises:
      at least one measuring chamber which has two wall parts located opposite one another, at least one of the wall parts being locally transparent, at least one of the wall parts being sufficiently deformable to facilitate displacement of the whole blood sample from the at least one measuring chamber for photometric analysis,
      the at least one measuring chamber further including a transparent body disposed between the wall parts, the transparent body being capable of selectively absorbing the analyte or reacting with the analyte such that upon contact of the analyte with the transparent body, a detectable change in a radiation transmission characteristic of the transparent body occurs which is dependent upon the concentration of the analyte in the whole blood sample, wherein the transparent body maintains the changed radiation transmission characteristic after displacement of the whole blood sample from the at least one measuring chamber so that photometric analysis of the analyte in the absence of the whole blood sample can be performed;
   b) placing the sampling device in a sampling device station wherein the sampling device station is arranged relative to an optical system comprising a radiation source and a means for detecting radiation, such that the sampling device is located between the radiation source and the radiation detection means;
   c) deforming the at least one measuring chamber of the sampling device in a controlled manner to reduce the volume of the at least one measuring chamber, thereby substantially draining the sample of whole blood from the measuring chamber;
   d) transmitting radiation from the radiation source through the deformed, substantially drained at least one measuring chamber to the radiation detector;
   e) detecting the radiation transmitted in step d); and
   f) determining the analyte content of the sample of whole blood from the radiation detected in step e).

10. A measuring chamber for photometric determination of the content of an analyte in a sample of whole blood, comprising:
   two wall parts located opposite one another, at least one of the wall parts being locally transparent, at least one of the wall parts being sufficiently deformable to facilitate displacement of the whole blood sample from the measuring chamber for photometric analysis,
   the measuring chamber further including a transparent body disposed between the wall parts, the transparent body being capable of selectively absorbing the analyte or reacting with the analyte such that upon contact of the analyte with the transparent body, a detectable change in a radiation transmission characteristic of the transparent body occurs which is dependent upon the concentration of the analyte in the whole blood sample, wherein the transparent body maintains the changed radiation transmission characteristic after displacement of the whole blood sample from the at least one measuring chamber so that photometric analysis of the analyte in the absence of the whole blood sample can be performed.

11. An analyzer for photometric determination of the content of an analyte in a sample of whole blood, comprising:
   a) a radiation source;
   b) means for detecting radiation transmitted from the radiation source;
   c) at least one measuring chamber which has two wall parts located opposite one another, at least one of the wall parts being locally transparent, at least one of the two wall parts being sufficiently deformable to facilitate displacement of the whole blood sample from the at least one measuring chamber for photometric analysis,
      the at least one measuring chamber further including a transparent body disposed between the wall parts, the transparent body being capable of selectively absorbing the analyte or reacting with the analyte such that upon contact of the analyte with the transparent body, a detectable change in a radiation transmission characteristic of the transparent body occurs which is dependent upon the concentration of the analyte in the whole blood sample, wherein the transparent body maintains the changed radiation transmission characteristic after displacement of the whole blood sample from the at least one measuring chamber so that photometric analysis of the analyte in the absence of the whole blood sample can be performed,
      wherein the at least one measuring chamber is arranged relative to the radiation source and the radiation detection means so that the radiation transmitted from the radiation source will pass through the at least one measuring chamber to the radiation detection means; and
   d) means for deforming at least one of the wall parts of the at least one measuring chamber in a controlled manner to reduce the volume of the at least one measuring chamber such that the sample of whole blood is substantially drained from the at least one measuring chamber.

12. A method of photometric in vitro determination of the content of an analyte in a sample of whole blood, comprising the steps of:
   a) transferring a sample of whole blood to a measuring chamber which has two wall parts located opposite one another, at least one of the wall parts being locally transparent, at least one of the wall parts being sufficiently deformable to facilitate displacement of the whole blood sample from the measuring chamber for photometric analysis,
      the measuring chamber further including a transparent body disposed between the wall parts, the transparent body being capable of selectively absorbing the analyte or reacting with the analyte such that upon contact of the analyte with the transparent body, a detectable change in a radiation transmission characteristic of the transparent body occurs which is dependent upon the concentration of the analyte in the whole blood sample, wherein the transparent body maintains the changed radiation transmission characteristic after displacement of the whole blood sample from the measuring chamber so that photometric analysis of the analyte in the absence of the whole blood sample can be performed, the measuring chamber being arranged relative to an optical system comprised of a radiation source and a means for detecting radiation such that the measuring chamber is located between the radiation source and the radiation detection means;

b) deforming the measuring chamber in a controlled manner to reduce the volume of the measuring chamber thereby substantially draining the sample of whole blood from the measuring chamber;

c) transmitting radiation from the radiation source through the deformed, substantially drained measuring chamber to the radiation detector;

d) detecting the radiation transmitted in step c); and e) determining the analyte content of the sample of whole blood from the radiation detected in step d).

* * * * *